US00PP31120P3

(12) United States Plant Patent
Sakazaki

(10) Patent No.: US PP31,120 P3
(45) Date of Patent: Nov. 26, 2019

(54) ***HYDRANGEA* PLANT NAMED 'USHYD0405'**

(50) Latin Name: ***Hydrangea* hybrid**
Varietal Denomination: USHYD0405

(71) Applicant: Plant 21 LLC, Bonsall, CA (US)

(72) Inventor: Ushio Sakazaki, Shiga (JP)

(73) Assignee: Plant 21 LLC, Bonsall, CA (US)

( * ) Notice: Subject to any disclaimer, the term of this patent is extended or adjusted under 35 U.S.C. 154(b) by 0 days.

(21) Appl. No.: 15/932,861

(22) Filed: May 9, 2018

(65) Prior Publication Data

US 2019/0037753 P1 Jan. 31, 2019

(30) Foreign Application Priority Data

Sep. 3, 2017 (QZ) ..... PBR 2017/1883

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ... A01H 5/02; A01H 5/00; A01H 6/48; A01H 1/02
See application file for complete search history.

(56) References Cited

PUBLICATIONS

Galopin et al. Architectural Development of Inflorescence in *Hydrangea macrophylla* cv. Hermann Dienemann. HortScience 43(2): 361-365, 2008. (Year: 2008).*

Upov Pluto Plant Variety Database Mar. 29, 2019 for *Hydrangea* Ushyd0405, retrieved on Apr. 10, 2019, retrieved from the Internet at https://www3.wipo.int/pluto/user/en/index.jsp, one page. (Year: 2019).*

* cited by examiner

*Primary Examiner* — June Hwu

(57) ABSTRACT

A new cultivar of *Hydrangea* plant named 'USHYD0405' that is characterized by inflorescences that arise from both terminal and lateral buds, white flowers, early flowering and small green leaves.

1 Drawing Sheet

Botanical classification: *Hydrangea* hybrid.
Variety denomination: 'USHYD0405'.

BACKGROUND OF THE INVENTION

The present invention relates to a new and distinct cultivar of *Hydrangea* plant botanically known as *Hydrangea* hybrid and hereinafter referred to by the cultivar name 'USHYD0405'.

The new cultivar is the product of a breeding program conducted by the inventor in a cultivated area of Higashiomi, Japan. The objective of the breeding program was to develop new *Hydrangea* cultivars that have attractive flower shapes and colors.

'USHYD0405' originated from the crossing in 2010 of the female or seed parent *Hydrangea macrophylla* 'Hobella' (U.S. Plant Pat. No. 9,462) and the male or pollen parent an unnamed proprietary *Hydrangea* cultivar. The cultivar 'USHYD0405' was selected by the inventor in 2013 as a single plant within the progeny of the stated cross in a cultivated area of Higashiomi, Japan.

Asexual reproduction by stem cuttings of the new cultivar 'USHYD0405' was first performed in 2013 in Higashiomi, Japan. Since that time, under careful observation, the unique characteristics of the new *Hydrangea* cultivar have been uniform, stable and reproduced true to type in successive generations of asexual reproduction.

SUMMARY OF THE INVENTION

The following represent the distinguishing characteristics of the new *Hydrangea* cultivar 'USHYD0405'. These traits in combination distinguish 'USHYD0405' as a new and distinct cultivar apart from other existing varieties of *Hydrangea* known to the inventor. 'USHYD0405' has not been tested under all possible conditions and phenotypic differences may be observed with variations in environmental, climatic, and cultural conditions, however, without any variance in genotype.

1. *Hydrangea* 'USHYD0405' exhibits inflorescences that arise from both terminal and lateral buds.
2. *Hydrangea* 'USHYD0405' exhibits white flowers.
3. *Hydrangea* 'USHYD0405' exhibits early flowering.
4. *Hydrangea* 'USHYD0405' exhibits small green leaves.

The closest comparison plants are *Hydrangea* 'Blue Wave' (not patented) and *Hydrangea* 'PIIHM-I' (U.S. Plant Pat. No. 20,176). The new cultivar 'USHYD0405' is distinguishable from 'Blue Wave' in the following characteristics:

1. 'USHYD0405' exhibits inflorescences that arise from both terminal and lateral buds. In contrast, the inflorescences of 'Blue Wave' arise only from terminal buds.
2. *Hydrangea* 'USHYD0405' exhibits white flowers. In contrast, the flowers of 'Blue Wave' are blue.
3. *Hydrangea* 'USHYD0405' exhibits smaller leaves than the leaves of 'Blue Wave'.
4. *Hydrangea* 'USHYD0405' exhibits earlier flowering than 'Blue Wave'.

The new cultivar 'USHYD0405' is distinguishable from 'PIIHM-I' in the following characteristics:

1. 'USHYD0405' exhibits inflorescences that arise from both terminal and lateral buds. In contrast, the inflorescences of 'PIIHM-I' arise only from terminal buds.
2. *Hydrangea* 'USHYD0405' exhibits white flowers. In contrast, the flowers of 'PIIHM-I' are pink.
3. *Hydrangea* 'USHYD0405' exhibits smaller leaves than the leaves of 'PIIHM-I'.
4. *Hydrangea* 'USHYD0405' exhibits earlier flowering than 'PIIHM-I'.

The new cultivar 'USHYD0405' is distinguishable from the female parent plant in the following characteristics:

1. 'USHYD0405' exhibits inflorescences that arise from both terminal and lateral buds. In contrast, the inflorescences of the female parent plant arise only from terminal buds.
2. *Hydrangea* 'USHYD0405' exhibits white flowers. In contrast, the flowers of the female parent plant are light pink.
3. *Hydrangea* 'USHYD0405' exhibits smaller leaves than the leaves of the female parent plant.
4. *Hydrangea* 'USHYD0405' exhibits earlier flowering than the flowers of the female parent plant.

The new cultivar 'USHYD0405' is distinguishable from the male parent plant in the following characteristics:

1. *Hydrangea* 'USHYD0405' exhibits larger leaves than the leaves of the male parent plant.
2. *Hydrangea* 'USHYD0405' exhibits larger flowers than the flowers of the male parent plant.

BRIEF DESCRIPTION OF THE DRAWING

The accompanying photograph illustrates the distinguishing traits of *Hydrangea* 'USHYD0405'. The plant in the photograph shows an overall view of a 12 month old glass greenhouse grown plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Hydrangea* cultivar named 'USHYD0405'. Data was collected in Heidesheim, Germany from 12 month old glass greenhouse grown plants in 16 cm. containers. The time of year was July and the temperatures ranged from 26-30° Centigrade during the day and 16-22° Centigrade during the night. The light level was natural outdoor light and there were no photoperiodic treatments or growth retardants used. Color determinations are in accordance with The Royal Horticultural Society Colour Chart, 2007 edition, except where general color terms of ordinary dictionary significance are used. The growing requirements are similar to the species.

Botanical classification: *Hydrangea* hybrid 'USHYD0405'.

Parentage: 'USHYD0405' resulted from the crossing of the female or seed parent *Hydrangea* 'Hobella' and the male or pollen parent an unnamed proprietary *Hydrangea* cultivar.

Annual or perennial: Perennial.

Plant type: Shrub.

Suitable container size: 14 cm. and larger.

Plant shape: Globe shaped.

Growth habit: Upright with spreading lateral branches.

Height: Average 50.0 cm.

Width: Average 100.0 cm.

Vigor: Strong.

Growth rate: Moderate.

Low temperature tolerance: −20 degrees Centigrade.

High temperature tolerance: 35 degrees Centigrade.

Propagation: Vegetative cuttings.

Time to initiate roots: 16 days are required to initiate roots at 22 degrees Centigrade in the summer.

Time to produce a rooted plant: 30 days are required to produce a rooted plant at 22 degrees Centigrade in the summer.

Crop time: Approximately 12 months are required to achieve a finished plant.

Root system: Main roots moderately thick, other roots moderately fine.

Stem:

*Branching habit.*—Free branching.
*Basal branching.*—Yes.
*Average number of lateral branches per plant.*—16.
*Pinching.*—Yes, pinching will improve branching.
*Lateral branch diameter.*—Average 6 mm. in diameter.
*Lateral branch length.*—Average 38.0 cm. in length.
*Internode length.*—Approximately 6.0 cm. between nodes.
*Stem shape.*—Round.
*Stem luster.*—Moderately glossy.
*Stem aspect.*—Average angle 37.5 degrees from vertical.
*Stem strength.*—Moderately strong.
*Stem fasciation.*—Absent.
*Lenticels.*—Absent.
*Stem color.*—145B, flushed with N170C.
*Stem pubescence.*—Absent.

Foliage:

*Leaf arrangement.*—Opposite.
*Compound or single.*—Single.
*Quantity of leaves per lateral branch.*—Average 12.
*Leaf shape.*—Elliptic.
*Leaf tip.*—Apiculate.
*Leaf base.*—Attenuate.
*Leaf margin.*—Crenate/serrate.
*Leaf dimensions.*—Length 12.0 cm; width 6.0 cm.
*Leaf texture (both sides).*—Smooth.
*Leaf luster.*—Upper surface slightly glossy, bottom surface matte.
*Leaf pubescence (both sides).*—Absent.
*Vein pattern.*—Pinnate.
*Leaf color young, upper surface.*—N137C.
*Leaf color young, lower surface.*—144A.
*Leaf color mature, upper surface.*—N137B.
*Leaf color mature, lower surface.*—144B.
*Vein color, upper side.*—144A.
*Vein color, under side.*—144D.
*Leaf attachment.*—Petiolate.

Petiole:

*Petiole dimensions.*—13 mm. in length and 2 mm. in diameter.
*Petiole texture.*—Smooth.
*Petiole pubescence.*—Absent.
*Petiole color.*—144D.

Inflorescence:

*Inflorescence type.*—Compound corymb, with sterile and fertile flowers, sterile flowers arranged in a single whorl.
*Inflorescence height.*—8.5 cm.

*Inflorescence width.*—13.5 cm.
*Quantity of flowers per inflorescence.*—Sterile 8 to 10; Fertile 330.
*Natural flowering season.*—April to June, sporadic to September in Germany.

Sterile flower buds:
*Bud dimensions.*—3.0 mm. in length and 2.0 mm. in diameter.
*Bud shape.*—Ovoid.
*Bud texture.*—Smooth.
*Bud pubescence.*—Absent.
*Bud color.*—145D.

Fertile flower buds:
*Bud dimensions.*—0.3 mm. in length and 0.2 mm. in diameter.
*Bud shape.*—Ovoid.
*Bud texture.*—Smooth.
*Bud pubescence.*—Absent.
*Bud color.*—145B.

Flower:
*Flower type.*—Fertile rotate; sterile cruciform.
*Flower aspect.*—Outward to upright.
*Flowering habit.*—Freely.
*Fragrance.*—None.
*Flower dimensions.*—Fertile 1.0 mm. in diameter and 4.0 mm. in height; Sterile 50 mm. in diameter and 5 mm. in height.
*Flower longevity.*—Sterile 4 to 6 weeks, fertile 10 to 14 days.
*Persistent or self-cleaning.*—Sterile persistent, fertile self-cleaning.

Sterile floret sepals:
*Number of sepals.*—4.
*Fused or un-fused.*—Not fused.
*Sepal overlapping.*—Medium.
*Dimensions.*—2.5 cm. in length and 2.5 cm. in width.
*Margin.*—Shallow crenate.
*Apex.*—Obtuse.
*Base.*—Obtuse.
*Texture.*—Smooth both sides.
*Color when opening* (*upper side*).—145D.
*Color when opening* (*under side*).—145D.
*Color fully opened* (*upper side*).—155B, tinged 56D.
*Color fully opened* (*under side*).—155B, tinged 56D.
*Color fading to.*—56D.

Fertile floret petals:
*Number of petals.*—5.
*Fused or un-fused.*—Not fused.
*Dimensions.*—3.0 mm. in length and 2.0 mm. in width.
*Margin.*—Entire.
*Apex.*—Cuspidate.
*Base.*—Acuminate.
*Texture.*—Smooth both sides.
*Color when opening* (*upper side*).—NN155B.
*Color when opening* (*under side*).—NN155B.
*Color fully opened* (*upper side*).—NN155C.
*Color fully opened* (*under side*).—NN155C.
*Color fading to.*—NN155C.

Fertile floret sepals:
*Sepal arrangement.*—Rotate.
*Number of sepals.*—5.
*Sepal dimensions.*—2.0 mm. in length and 2.0 mm. in width.
*Sepal shape.*—Ovate.
*Sepal apex.*—Apiculate.
*Sepal base.*—Fused.
*Sepal margin.*—Entire.
*Sepal texture* (*both sides*).—Smooth.
*Sepal color, young* (*upper side*).—138B.
*Sepal color, young* (*under side*).—138B.
*Sepal color, mature* (*upper side*).—138B.
*Sepal color, mature* (*under side*).—138B.

Peduncle:
*Peduncle dimensions.*—1.25 cm. in length and 1.0 mm. in diameter.
*Peduncle angle.*—45 degrees from lateral branch axis.
*Peduncle strength.*—Moderately strong.
*Peduncle texture.*—Smooth.
*Peduncle color.*—145A.

Pedicels:
*Pedicel dimensions.*—5.0 mm. in length and 0.5 mm. in diameter.
*Pedicel angle.*—45 degrees from peduncle axis.
*Pedicel strength.*—Moderately strong.
*Pedicel texture.*—Smooth.
*Pedicel color.*—145A.

Reproductive organs:
*Stamen number.*—8 to 9.
*Anther shape.*—Basifixed.
*Anther dimensions.*—0.8 mm. in length and 0.3 mm. in width.
*Anther color.*—4D.
*Amount of pollen.*—Moderate.
*Pollen color.*—4D.
*Number of pistils.*—1.
*Pistil length.*—2.0 mm.
*Stigma shape.*—Funnel shaped.
*Stigma color.*—NN155B.
*Style length.*—1.0 mm.
*Style color.*—NN155B.
*Ovary color.*—NN155B.

Fruit and seed production: Fruit and seed development has not been observed to date.

Disease and pest resistance: Disease and pest resistance has not been observed to date.

The invention claimed is:

1. A new and distinct variety of *Hydrangea* plant named 'USHYD0405' as described and illustrated.

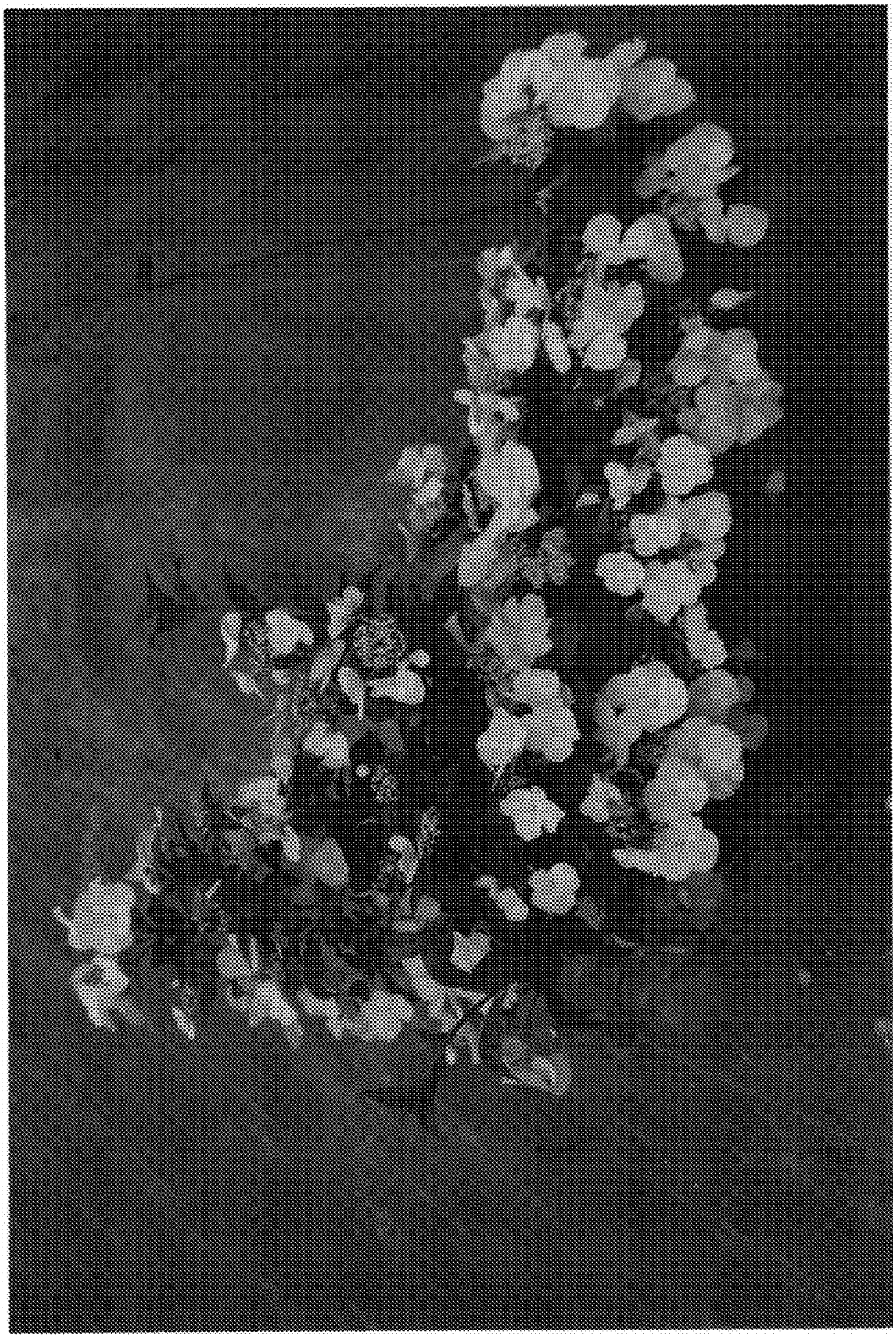

* * * * *